United States Patent [19]
Barry et al.

[11] Patent Number: 5,266,326
[45] Date of Patent: Nov. 30, 1993

[54] IN SITU MODIFICATION OF ALGINATE

[75] Inventors: James J. Barry, Woburn, Mass.; Paul A. Higham; Harold M. Aberman, both of Ringwood, N.J.

[73] Assignee: Pfizer Hospital Products Group, Inc., New York, N.Y.

[21] Appl. No.: 906,953

[22] Filed: Jun. 30, 1992

[51] Int. Cl.[5] .................. A61F 2/02; A61K 9/14; A61K 47/36; C08B 37/04
[52] U.S. Cl. .................. 424/423; 424/488; 514/779; 536/3; 604/51; 604/56
[58] Field of Search ............ 536/3; 424/423, 444, 424/488; 604/51, 56; 514/779

[56] References Cited

U.S. PATENT DOCUMENTS

| | | | |
|---|---|---|---|
| 4,572,906 | 2/1985 | Sparkes et al. | 514/21 |
| 4,994,277 | 2/1991 | Higham et al. | 424/423 |
| 5,093,319 | 3/1992 | Higham et al. | 424/444 |

*Primary Examiner*—Thurman K. Page
*Assistant Examiner*—C. Azpuru
*Attorney, Agent, or Firm*—Peter C. Richardson; Lawrence C. Akers; Raymond W. Augustin

[57] ABSTRACT

A method of modifying salts of alginic acid in situ for prevention and treatment of various intra-articular and extra-articular (spine) complications modifies the alginate in situ to an insoluble gel. This in situ modification provides a final product which can be compressed within the intra-articular space thus remaining localized. The modified material can have varied mechanical strengths and thus varied degradation times and can serve as a matrix for localizing and slowly releasing therapeutic agents. The modified material is biocompatible and biodegradable, thus requiring no reoperation for removal.

12 Claims, No Drawings

IN SITU MODIFICATION OF ALGINATE

BACKGROUND OF THE INVENTION

1. Field of the Invention

This invention relates to a material which can be placed into intra-articular spaces to serve primarily as a space occupier for post-operative intra-articular adhesions. More specifically, it relates to a biocompatible and biodegradable material which is modified while in the intra-articular space (in situ) to prevent adhesions formed post-operatively.

2. Description of the Prior Art

Alginic acid was first purified from seaweed in 1896 (British Patent No. 11,538), and was subsequently commercialized in 1954 by Kelco (Advan. Chem. Ser. No. 11., American Chemical Society, Washington, D.C., pp. 68–82). Alginic acid, the polysaccharide extracted from the seaweed, is composed of segments of D-mannuronic acid units, L-guluronic units, and segments of alternating mannuronic and guluronic units. This polysaccharide is most commonly used to thicken solutions, stabilize suspensions and emulsions, gel various mixtures, and form films on various surfaces. Although alginic acid is water insoluble, the sodium salt of alginic acid, sodium alginate, is water soluble.

One of the most desirable properties of sodium alginate is its ability to complex and form strong gels with divalent cations such as calcium. Calcium alginate gels are water insoluble. There is a correlation between the strength of the calcium alginate gel and the guluronic acid content of the sodium alginate. Because of this characteristic, alginate has been established as a versatile biopolymer for use in various biomedical applications. Commercially available wound dressings, such as Kaltostat (BritCair Ltd.) and Sorbsan (Steriseal Ltd.), have been manufactured from fibers of calcium alginate. Extensive research is being conducted in the area of creating artificial organs by entrapping cells within calcium alginate beads and implanting them in the body. This same technology has been utilized in the drug delivery field. A good example of the use of this encapsulation technology is outlined in U.S. Pat. No. 4,744,933 by Rha in 1988. As early as 1947, George Blaine presented the idea of using calcium alginate as a method of preventing adhesions in the surgery of nerves and tendons (Blaine, The Medical Press, Aug. 20, 1947, p. 166). Subsequently, sodium alginate solution was shown to be effective in prevention of adhesions in the peritoneal cavity following laparotomy procedures (Japanese Patent SH057-167919). More recently, ester derivatives of sodium alginate have been developed and mentioned as potential anti-adhesions materials (European Patent Application 0 251 905). However, none of these patents or studies teach a simple in situ method of complexing alginate to prevent intra-articular adhesions and other intra-articular complications.

Adhesions result from the organization of fibrinous exudate on tissue surfaces due to the infliction of trauma or inflammation. Vital tissues such as blood vessels, or organs including the kidney, liver, and intestines are coated with mucous or serous membranes so that they can function independently of each other. Examples of these mucous or serous membranes are the body wall pleura and the organ pleura in the thoracic cavity and the parietal peritoneum and mesentery in the abdominal cavity, each protecting the corresponding organs. Surgical trauma or inflammation in those portions of the body coated with serous membranes may result in the build up of fibrinous exudate regardless of the size of the affected part. This ultimately causes the creation of organized fibrin many times referred to as scarring or adhesions. Such adhesions between these tissues may be observed in all tissues of the body, not just those mentioned above. Fibrinous adhesions between tissues can lead to severe pain, decreased function, and even permanent loss of motility.

In the orthopaedics field, conditions such as acute or chronic arthritis (e.g. suppurative arthritis, rheumatoid arthritis, gonorrheal arthritis, tuberculous arthritis), or traumatic injuries at the joint (e.g. fracture, sprain) would result in ankylotic diseases wherein the surface of the bones constituting the joint adhere to each other and thereby restrict the mobility of the joint. Congenital radioulnar syntosis wherein a spoke bone and an ulna adhere together is difficult to remedy by a surgical operation, since the separated bones would frequently re-adhere.

Adhesions are also prominent in tendon surgery. In this instance, there is a general tendency towards adhesion between the tendon and the surrounding sheath or other surrounding tissue during an immobilization period following the operation (P. Matthews et al, JBJS vol. 58B, no. 2, p. 230, 1976, Matthews, The Hand, vol. 11, no. 3, p. 233, 1979, Gelberman et al, Hand Clinics, vol. 1, no. 1, p. 35, 1985).

Recently, there has been a resurgence of interest in the prevention of the "laminectomy membrane" which forms following spinal laminectomy procedures. The laminectomy membrane is a well organized mass of fibrinous tissue which replaces the bone that was removed at the laminectomy. This fibrinous mass binds the dura to the overlying muscles (H. LaRocca and I. McNab, JBJS, vol. 56B, no. 3. p. 545, 1974) and causes narrowing of the spinal canal which places pressure on the cauda equina or nerve roots. This scar tissue formation may require reoperation which is tedious and dangerous, leading to the possibility of dural tears and damage to the emergent nerve roots resulting in motor weakness, sensory change and painful paresthesia.

The present invention also addresses the prevention of adhesions in the intra-articular spaces. While complications of the patello-femoral joint following total knee replacement are rare, the dysfunction of the patello-femoral articulation has been found secondary to intra-articular fibrinous bands (Thorpe et al, JBJS vol. 72A, no. 6, p. 811, 1990). Intra-articular fibrosis in anterior cruciate ligament (ACL) reconstruction has also been identified as a problem (Shelbourne et al, Am. J. Sports Med., vol. 19, no. 4, p. 332, 1991).

The prior art teaches various treatments to prevent scar tissue build up. Treatments such as liquid paraffin, camphor oil, chondroitin sulfate, and urea exhibit an insufficient effect since they function only temporarily. Other prophylactic treatments such as silicone membranes, gutta percha, or poly(tetrafluoroethylene) membranes have been used to serve as barriers to adhesion formation. However, these materials are inert and will, therefore, remain in the body and many times be recognized as a foreign body. Therefore, a second operation may be necessary to remove the barrier material.

Chitosan and xanthan gum (U.S. Pat. Nos. 5,093,319 and 4,994,277) respectively, owned by the assignee of the present invention, also teach methods of preventing adhesions with polysaccharides. Neither of these patents, however, teach the use of in situ complexed alginate for the prevention of intra-articular adhesions.

The material of the present invention is an aqueous hydrogel which will dissolve over time in vital tissues. Since this material contains water, later hydrolysis is unnecessary. In the past, hydrogels have been used in adhesion applications, but they have either been covalently cross-linked to improve their lifetime and therefore have undesirably long degradation times, or else they did not last long enough in the site to be effective.

The adhesion prophylaxis of the present invention comprises a polymer which is biocompatible and biodegradable comprised of polysaccharide units which may be broken down by the body into simple sugars which are then metabolized. The half-life of the hydrogel material to be used in adhesion prevention can range from about two days up to one year in vivo. Therefore, it is possible to prevent adhesions by placing the adhesion preventative at the site where there is a fear of adhesion setting in. The period the prophylaxis stays in place depends on the rate of absorption by dissolution or degradation. The adhesion preventative made of the material of the present invention will disappear without requiring reoperation for its removal.

SUMMARY OF THE INVENTION

The object of this invention is to provide for a biodegradable/bioresorbable material capable of preventing the build up of fibrinous exudate between adjacent tissues resulting from surgery.

It is another object to provide a material which can be easily modified during the application of the material to the site of trauma.

It is still another object of this invention to provide a material which can be easily applied after the surgical site has been closed, or just prior to closing the surgical site.

Accordingly, these and related objects are achieved by placing the sodium alginate solution between the affected tissues and modifying it to prevent a fibrinous binding, i.e. adhesion, of the tissues. This can be accomplished by simultaneous injection of the alginate solution and a complexing solution such as calcium chloride into the intra-articular space following closure of the surgical site. This can be accomplished with injection via separate syringes or via a signle double barrel syringe with either a concentric needle or a double lumen needle. If necessary, the alginate solution could be applied to the site prior to closing followed by addition of the complexing solution.

These and other objects and advantages of the present invention will become apparent from the following detailed description which discloses several embodiments of the invention. It is to be understood that the examples are for the purposes of illustration only, and not as a definition of the invention.

DESCRIPTION OF THE PREFERRED EMBODIMENT

The biodegradable/bioresorbable hydrogel polymers of the present invention prevent adhesions, i.e. inhibit fibrin formation and organization between tissues. These materials are materials which will eventually revert to the gel or solution state and ultimately be resorbed and safely metabolized by the body. Examples of such polymer materials include naturally occurring polysaccharides such as alginate.

Alginic acid is a linear copolymer of (1-4) -linked beta-D-mannuronic acid (M) and its C-5 epimer, alpha-L-guluronic acid (G). The salt forms (and esters) of this polysaccharide are generally named alginates. It has been shown that the G- and M-units are jointed together in a block-wise fashion. This implies that three types of blocks may be found, homopolymeric G-blocks, homopolymeric M-blocks, and heteropolymeric, sequentially alternating blocks.

Alginate is a polymerized dimer made up of salts of guluronic acid and mannuronic acid (guluronate and mannuronate), which are epimers of each other. Depending on the source from which the alginate was extracted, its composition can vary from primarily guluronakte (in the case of alginate extracted from the stems of the seaweed, Laminaria hyperborea) to primarily mannuronate (extractyed from laminaria japonica).

The chemical composition of alginate is to a certain extent variable and diverse. It varies between seaweed species, between different parts of the same plant, and is subject to seasonal changes. Nevertheless, by seletion of raw materials with different properties, it is possible to manufacture a variety of alginates with constant characteristics.

For example, the mannuronate/guluronate ratio and how the block copolymer is arranged determines the polymer's physical properties, such as gel strength and film forming capabilities. The strongest films come from alginates with large amounts of guluronate-guluronate blocks (high G); whereas, the best thickening agents come from alginates with large amounts of mannuronate-mannuronate blocks (high M). Alginates are available commercially. An example of a high G alginate is Protan Lab's HF 120, and an example of a high M alginate is Protan's HF 120 RB. By adjusting the ratios of the blocks of the two polymers, the physical properties can be adjusted to meet the application of interest.

Among these starting materials it is preferable to use water soluble polymers which have not been cross-linked to form insoluble materials. It has been found advantageous to use polymers which can be temporarily insolubilizd by non-toxic ionic bridges to form substances which will begin to degrade in a period of 2-5 days up to one year. In order to vary the degradation time, the amount of cross-linking can be varied.

Specific examples of these polymers include: sodium alginate, alginic acid, calcium alginate, magnesium alginate, potassium alginate, or monovalent alginate salts complexed with divalent or multivalent cations. The molecular weight of these biodegradable polymers for use in the present invention preferably can range from 1,000 daltons to 3,000,000 daltons. The concentration of solutions of these polymers, such as sodium alginate, used herein are from about 0.1% to 4%.

It is possible to prevent adhesions by simultaneously injecting the alginate with a complexing agent to form a material which is more viscous and elastic than blood so that it prevents blood from clotting at the interface of two vital tissues, thus preventing an adhesion from forming.

The invention will now be described in further detail with reference being made to the following examples. It should, however, be recognized that the examples are given as being illustrative of the present invention and are not intended to define the spirit and scope thereof.

EXAMPLE 1

A sterile 1.6% solution of high G sodium alginate in 0.9% saline is obtained from Protan Labs (Pronova LV G) via Irvine Scientific. The solution has a pH of 7.02, an osmolarity of 311 mosm/kg water, and an endotoxin content less than 1.2 EU/ml as determined by Limulus Amoebocyte Lysate (LAL). 0.5 cc of this solution is injected into each of 4 stifle joints of two New Zealand White rabbits (NZW). After 2 and 4 days one rabbit is sacrificed and the stifle opened for gross evaluation, cytological evaluation, and histological evaluation. At two days the sodium alginate is grossly present in the stifle joint. The majority of the material appeared in the posterior pouch. Material is also noticed in the long digital extensor sheath. Neither cytology of the synovial fluid nor histology indicated any adverse reaction of the tissue to the sodium alginate. At 4 days post op, there is no gross indication of any material present in the stifle. Cytological evaluation indicates no adverse reaction to the material. Histology indicates no adverse reaction to the material, and shows a coating of the sodium alginate over the tissue sections analyzed (synovial membranae, articular cartilage, and ACL).

EXAMPLE 2

A 0.25% solution is prepared by addition of 5 grams of sodium alginate (Pronova MV G, Protan) to 2 liters of 0.15M PBS. The resulting solution is filtered through a 0.45/0.22 micron filter capsule (Sartorius). The solution is then filtered through a 0.2 micron Endotoxin Affinity Membrane (EAM) (AlerCHEK, Portland, Me.) via a tangential flow process. Both the filtrate and retenate are subsequently collected and the equipment depyrogenated. This procedure is repeated for ten cycles. Following the tenth cycle, the solution (approximately 1.9 liters) is then rendered free of all low molecular weight impurities by extensive dialysis (ten cycles—pump down to 300 ml and reconstituted to 1,900 ml) with 0.5% saline via a 30K molecular weight cutoff membrane (Filtron, Norwood, Mass.) on the same ultrafiltration equipment. On the final pump down step the material is concentrated to 118 ml (4% alginate in 0.5% saline) and sterile filtered through a 0.22 micron membrane. Pyrogen concentration is determined to be 6.3 EU/ml in a 4% solution. A 4 day intra-articular injection of 0.5 cc of the purified materials is conducted in two stifle joints of a NZW. Evaluation of the tissues via gross, cytology, and histology indicated no adverse reaction to the material.

To test the adhesive prevention ability of the alginate, the fat pad from the stifle joint of the rabbit is removed and the tibia abrased. The joint is immobilized for 21 days. Two NZW rabbits serve as controls and are injected with 0.9% saline following closure. Three other animals are injected with the sodium alginate solution prepared in Example 2. All three are injected with 0.5 cc at closure (time 0). One is reinjected with 0.5 cc of the alginate solution at 7 days post op (time 0 and 7) and the third is injected at 4, 8, and 12 days post op (time 0, 4, 8, 12). All five animals are sacrificed at 21 days. Control animals show excellent adhesion formation upon gross and histological evaluation. Results of adhesions from the control subjects indicate no difference in quality or quantity of adhesion formed upon gross evaluation or histological evaluation when compared to the treated knee. Histology indicates that sodium alginate is present coating the tissues in all three test subjects. These results indicate that a thin coating of only the alginate material is not sufficient to prevent or reduce intra-articular adhesions.

EXAMPLE 3

A complexing solution is now utilized to cross-link the alginates of Examples 1 and 2. Two NZW rabbits are used as test subjects. Injections are made into both stifle joints of the two rabbits. One stifle receives a simultaneous injection of 0.5 cc sodium alginate (Example 1) and 0.2 cc of 2% calcium chloride from two separate syringes placed within the stifle joint. A second joint receives simultaneous injection of 0.5 cc of 0.16% sodium alginate and 0.3 cc of 2% calcium chloride. A third stifle joint receives a simultaneous injection of 0.5 cc of sodium 0.16% alginate and 0.4 cc of 2% calcium chloride, and the final joint receives 0.5 cc of 0.16% alginate and 0.5 cc of 2% calcium chloride. The purpose of this is two-fold; 1) to determine the effect of different volumes of calcium chloride on gel strength in the joint and 2) evaluate the inflammatory response to the calcium alginate gel formed in situ. The gross evaluation at two days post op indicates no inflammatory reaction to any mixture. This is confirmed by cytology and histology. There appears to be a correlation between gel strength and gel presence with increasing calcium chloride volume. The 0.5 cc of calcium chloride also seems to produce a calcium alginate gel within the stifle which almost produces an impression of the joint.

The test for adhesion preventions set forth above is performed by injecting the four solutions of Example 3 into four prepared stifle joints of NZW rabbits. After twenty days the stifle joints of the rabbits are examined. In the first rabbit, the gel is still present in the joint. It is red in color from entrapping blood at the time of surgery. There are no adhesions and the joint surfaces and surrounding synovium look fine. Similar findings are seen in the second rabbit, except that the gel remains clear. A few thin adhesions from leftover hemorrhage are seen, but these break upon light touching with a probe. Again, the joint looks healthy. The material has spread out from beyond the region of the fat pad along the sides of the condyles. The material is friable but slippery. In comparison to the experience with fat pad replacement, it appears that the stifles from these animals are healthier and have less adhesions. Tissues and the stifle joint are then collected for histology.

The solutions of the present invention may be injected into joints other than the knee, such as the elbow, shoulder and also into the spine. Drugs or other therapeutic agents such as antibiotics or anti-inflammatory agents may be included in the solution.

In addition to calcium chloride, other water soluble cations may be used as the complexing solution such as $MgCl$, $CaSO_4$, $MgSO_4$, etc. Concentrations of these complexing solutions range from about 0.5% to 2%.

While several examples of the present invention have been described, it is obvious that many changes and modifications may be made thereunto, without departing from the spirit and scope of the invention. This includes first injecting the complexing solution and thereafter injecting the alginate solution.

We claim:

1. A method for preventing adhesions in situ between tissues after surgery comprising the steps of:

injecting a water soluble 0.1% to 4% alginate solution into the intra-articular space prior to or after closing the surgical site; and injecting a 0.5% to 2% complexing solution of water soluble cations into said intraarticular space.

2. The method for preventing adhesions as set forth in claim 1 wherein said alginate is selected from the group consisting of sodium alginate, alginic acid, calcium alginate, magnesium alginate, potassium alginate and a combination thereof.

3. The method for preventing adhesions between tissues as set forth in claim 2 wherein said alginate solution and said complexing solution are injected simultaneously.

4. The method for preventing adhesions as set forth in claim 2 wherein said step of simultaneously injecting said alginate solution and said complexing solution is done with a double lumen needle.

5. The method for preventing adhesions between tissues as set forth in claim 1 wherein said complexing solution is injected after said alginate solution is injected.

6. The method for preventing adhesions between tissues as set forth in claim 1 wherein said complexing solution is selected from the group consisting of magnesium chloride, calcium sulfate, calcium chloride and a combination thereof.

7. A method for preventing adhesions in situ between tissues comprising the steps of:

placing a water soluble 0.1% to 4% alginate solution between the tissues; and cross-linking the alginate by placing a 0.5% to 2% complexing solution of water soluble cations between the tissues.

8. The method for preventing adhesions as set forth in claim 7 wherein said alginate is selected from the group consisting of sodium alginate, alginic acid, calcium alginate, magnesium alginate, potassium alginate and a combination thereof.

9. The method for preventing adhesions between tissues as set forth in claim 7 wherein said alginate solution and said complexing solution are injected simultaneously.

10. The method for preventing adhesions as set forth in claim 7 wherein said step of simultaneously injecting said alginate solution and said complexing solution is done with a double lumen needle.

11. The method for preventing adhesions between tissues as set forth in claim 7 wherein said complexing solution is injected after said alginate solution is injected.

12. The method for preventing adhesions between tissues as set forth in claim 7 wherein said complexing solution is selected from the group consisting of magnesium chloride, calcium sulfate, calcium chloride and a combination thereof.

* * * * *